United States Patent [19]

Walinsky et al.

[11] Patent Number: 4,641,649
[45] Date of Patent: Feb. 10, 1987

[54] METHOD AND APPARATUS FOR HIGH FREQUENCY CATHETER ABLATION

[75] Inventors: Paul Walinsky, Philadelphia, Pa.; Arye Rosen, Cherry Hill, N.J.; Arnold J. Greenspon, Jenkintown, Pa.

[73] Assignee: RCA Corporation, Princeton, N.J.

[21] Appl. No.: 792,895

[22] Filed: Oct. 30, 1985

[51] Int. Cl.⁴ .............................................. A61N 1/32
[52] U.S. Cl. ........................... 128/303.1; 128/303.13; 128/804; 128/328; 128/784; 128/642
[58] Field of Search ................ 128/303.1, 303.13, 362, 128/328, 783, 784, 864

[56] References Cited

U.S. PATENT DOCUMENTS

| | | | |
|---|---|---|---|
| 3,789,834 | 2/1974 | Duroux | 128/734 |
| 4,240,445 | 12/1980 | Iskander et al. | 128/804 |
| 4,245,649 | 1/1981 | Schmit-Andersen | 128/804 |
| 4,291,707 | 9/1981 | Heilman et al. | 128/784 |
| 4,328,809 | 5/1982 | Hirschowitz et al. | 128/653 |
| 4,346,716 | 8/1982 | Carr | 128/804 |
| 4,409,993 | 10/1983 | Furihata | 128/784 |
| 4,432,369 | 2/1984 | Halvorsen | 128/653 |

OTHER PUBLICATIONS

Article, "Catheter Ablation in Dyrhythmias", by Paul C. Gillette, M.D., published in the Mar. 1984 issue of Cardio magazine, pp. 67-69.
Article, "Transvenous Catheter Ablation of a Posteroseptal Accessory Pathway in a Patient with Wolff-Parkinson-White Syndrome", by F. Morady, M.D. et al., published at pp. 705-707 of the Mar. 15, 1984, New England Journal of Medicine.
Article, "Effects of Laser Irradiation Delivered by Flexible Fiberoptic System on the Left Ventricular Internal Myocardium", by G. Lee, M.D. et al., published at pp. 587-590 of the Sep. 1983 issue of American Heart Journal.

*Primary Examiner*—Kyle L. Howell
*Assistant Examiner*—David Shay
*Attorney, Agent, or Firm*—Joseph S. Tripoli; Robert L. Troike; William H. Meise

[57] ABSTRACT

A medical procedure for treatment of tachycardia (rapid heartbeat) or cardiac disrhythmia uses a catheter which includes a flexible coaxial transmission line (coax) terminated by an antenna. The antenna and coax are introduced into a chamber of the heart. The antenna is brought into contact with a wall of the heart. Action potentials generated by the heart are coupled through the antenna and the coaxial cable to a standard electrocardiograph apparatus for display. Other electrodes placed about the body also produce action potentials which are displayed by the electrocardiograph. The position of the antenna in the chamber of the heart is adjusted with the aid of the displayed action potentials until the antenna is in contact with the region to be ablated or injured as indicated by its characteristic electrical signature. When the antenna is adjacent to or in contact with the desired location, radio frequency or microwave frequency electrical energy is applied to the proximal end of the coax and through the coax to the antenna. The action potentials may be viewed while the electrical energy is applied. The power of the electrical energy is slowly increased until the desired amount of blockage of the bundle of His or damage to the ectopic focus has been achieved.

6 Claims, 9 Drawing Figures

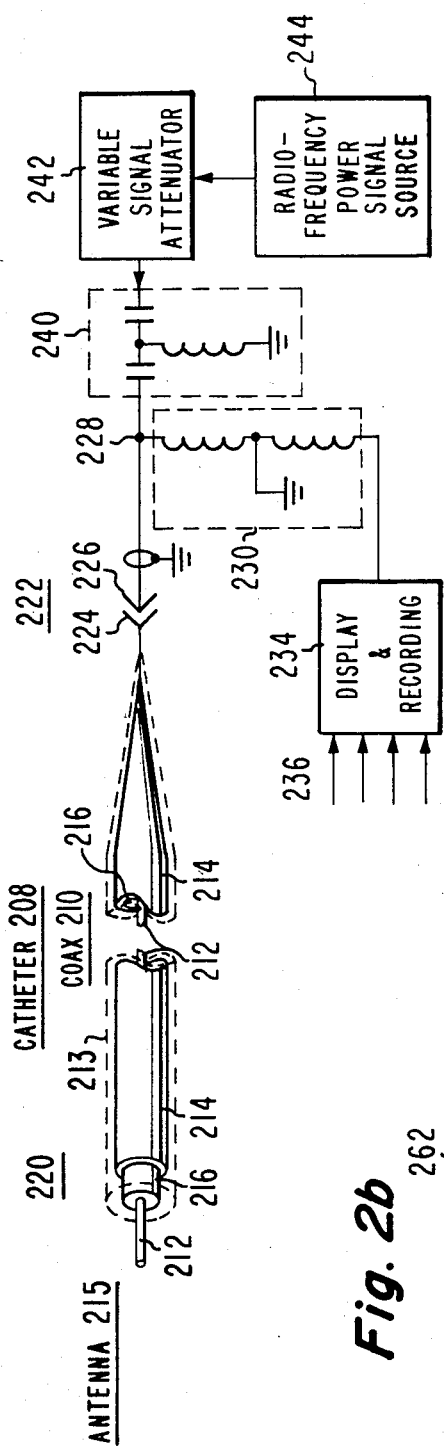
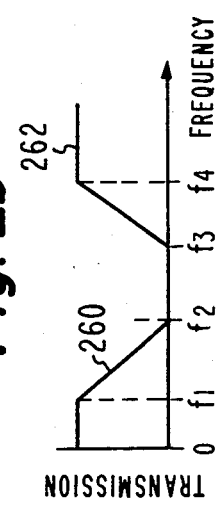
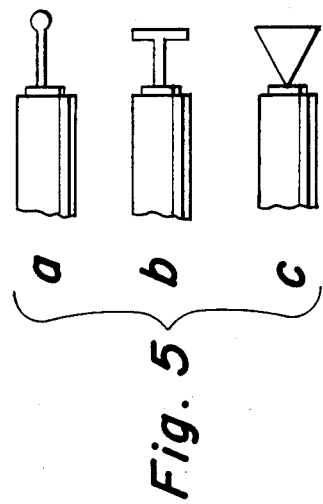
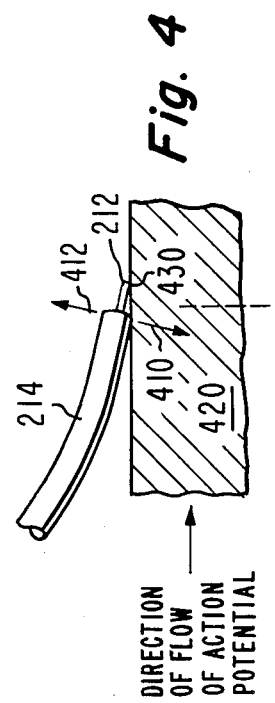

METHOD AND APPARATUS FOR HIGH FREQUENCY CATHETER ABLATION

BACKGROUND OF THE INVENTION

This invention pertains to medical ablation procedures and particularly to selective ablation of cardiac tissue by means of high-frequency electromagnetic energy.

The heart is composed of three types of cardiac tissue; atrial muscle, ventricular muscle and specialized excitatory and conduction tissues. The atrial and ventricular muscles of the heart are normally excited in synchrony. Each cardiac cycle begins with the generation of action potentials by the sino-atrial (SA) or sino-auricular node located in the posterior wall of the right atrium. These action potentials spread through the atrial muscle by means of specialized conduction tissue, causing contraction. The action potentials do not normally spread directly from the atrial muscles to the ventricular muscles. Instead, the action potentials conducted in the atrial musculature reach the atrioventricular (AV) node and its associated fibers, which receive and delay the impulses. Potentials from the AV node are conducted to the His-Purkinje bundle. This structure carries the impulses to the ventricular musculature to cause their synchronous contraction following contraction of the atrial muscles.

Episodes of an abnormal increase in heart rate may occur, and are termed paroxysmal tachycardia. This can result from an irritable focus in the atrium, the AV node, the bundle of His, or in the ventricles. These episodes of tachycardia may be initiated and sustained by either a re-entrant mechanism, termed a "circus" movement, or may be caused by repetitive firing of an isolated ectopic focus. While these episodes of tachycardia are usually amenable to treatment by medication, under certain circumstances surgical ablation of the abnormal focus of abnormally conducting tissue may be of value in selected instances.

Catheter techniques have been used for treatment of these tachycardias. As described in the article "Catheter Ablation in Dysrhythmias" by Gillette, published in the March 1984 issue of Cardio, standard electrophysiologic techniques involving multiple catheter recording and stimulation of the heart at several sites may be used to determine the mechanism of the cardiac dysrhymia. If pharmacological testing indicates that drugs are not useful in control of the arrhythmia, a standard intracardiac electrophysiologic catheter may be introduced and positioned adjacent to specialized conduction tissue responsible for the initiation or perpetuation of the arrythmia. The location of this tissue is usually the His bundle. Therefore, by positioning the catheter so that a His bundle electrogram is recorded, the electrode recording the His potential may then be connected to the output of a DC defibrillator. This defibrillator then delivering 3 to 5 watt-seconds per kilogram (wsec/kg) may be used to ablate that portion of the bundle of His adjacent to the electrode. This procedure may be useful in the treatment of selected cardiac arrythmias. Similarly, abnormal foci elsewhere in the heart may be treated by electrical ablation.

The Gillette procedure may be disadvantageous in the atrium, because the wall of the atrium is thin. The atrium may be perforated if the applied energy is excessive for the location. The amount of heart tissue injured by the ablating energy in this method may also undesirably exceed that which is necessary to achieve the desired ablation of the bundle of His or other ectopic focus. Furthermore, catheter ablation should be limited to the right atrium and right ventricle because of the danger of embolization due to gas or debris resulting from the procedure. Also, the application of energy from a defibrillator depolarizes the heart muscles and interrupts the normal cardiac cycle. This may be disadvantageous, especially when multiple applications of energy are required.

However, a catheter ablation procedure which is capable of reducing the amount of extraneous tissue damage during ablation, thereby reducing the danger of perforation, and which may be usable on the left side of the heart is desirable.

SUMMARY OF THE INVENTION

A treatment method and apparatus includes introducing into a chamber of the heart one end of a coaxial transmission line. The coaxial transmission line includes a center conductor and an outer conductor. The end of the coaxial transmission line introduced in the chamber of the heart is terminated in an antenna coupled to the center conductor. The position of the coaxial transmission line and associated antenna are adjusted to bring the antenna into contact with action potentials indicating contiguity to the desired location in the heart. A video system is coupled to the other end of the coaxial transmission line for displaying the action potentials. The position of the coaxial transmission line is further adjusted while monitoring the displayed action potentials to place the antenna contiguous with that point on the chamber wall having an electrical signature corresponding with the desired point. High frequency electromagnetic energy is applied to the end of the coaxial transmission remote from the heart. Sufficient energy is applied to injure or ablate tissue near the point. In one form of the method according to the invention, the selected location has the earliest action potential which drives a tachycardic heart. In another method according to the invention, the selected point is a point on the bundle of His which when ablated, prevents the perpetuation of the reentrant tachycardia.

DESCRIPTION OF THE DRAWING

FIG. 2a illustrates, partially in pictorial form, partially in schematic and partially in block forms an apparatus including a catheter and filters useful in a method according to the invention, and FIG. 2b is a plot of transmission versus frequency for filters of the arrangement of FIG. 2a;

FIG. 4 illustrates a preferred orientation of the end of the coaxial transmission line adjacent the point to be injured or ablated;

FIG. 5a-c illustrate various types of antennas terminating the coaxial transmission line;

DESCRIPTION OF THE DRAWING

Figure 1:
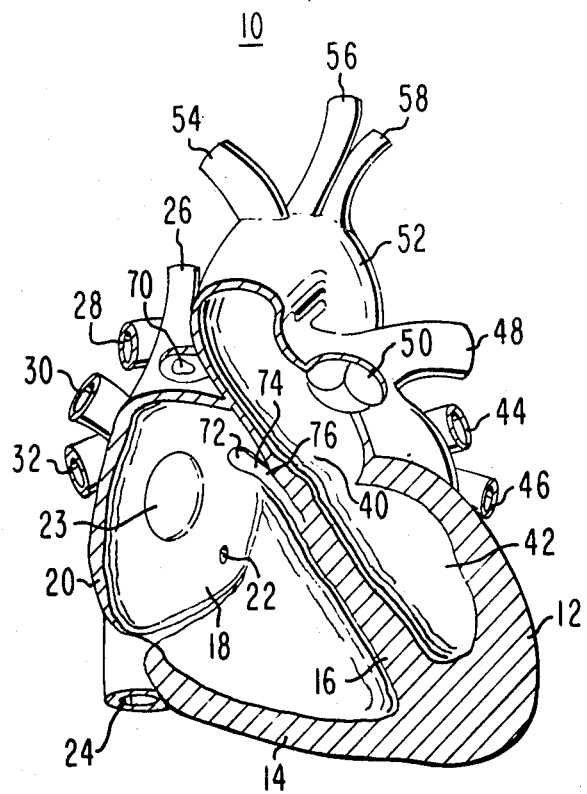
FIG. 1 is a sectional view of a human heart.

FIG. 1 is a simplified view of a heart 10, sectioned to show interior details. In FIG. 1, the muscular wall of the left ventricle is designated as 12, the muscular wall of the right ventricle is designated 14, and the ventricular septum is designated 16. The chamber of the right atrium 18 is surrounded by a wall of atrial muscle 20. The mouth 22 of the coronary sinus and the fossa ovale 23 are formed in portions of the wall of the right atrium. A portion of the inferior vena cava 24 located below and opening into chamber 18 of the right atrium, and a portion of the superior vena cava 26 opening into chamber 18 from above are sources of venous blood which are pumped by the right half of the heart to the lungs by paths including the right pulmonary artery 28. Oxygenated blood returning to the heart from superior and inferior pulmonary veins 30 and 32 is introduced to the chamber 40 of the left atrium. Also visible in FIG. 1 are the chamber 42 of the left ventricle, the left superior and inferior pulmonary veins 44 and 46, the left pulmonary artery 48 and its pulmonary valve 50, the aorta 52, the innominate artery 54, left carotid artery 56 and left subclavian artery 58. The sinoauricular (SA) node 70 is illustrated as being formed in the posterior wall of the vault of the atrium. Also located on the interior wall of the right atrium is the atrioventricular (AV) node 72 illustrated as being connected by a bundle of transitional fibers 74 to the atrioventricular bundle 76 of Purkinje fibers which coalesce with ventricular septum 16. The Purkinje fibers extend in right and left branches (not illustrated) through the muscles 12 and 14 of the left and right ventricles, and terminate within walls 12 and 14 in the sarcoplasmic reticulum of the ventricular muscle. The AV node 72, transitional fibers 74, and AV bundle 76 are known collectively as the bundle of His.

During normal operation of the heart, SA node 70 periodically generates action potentials which spread throughout the walls of the left and right atrium, and which result in contractions and blood pumping action by the atrial muscles. The action potentials approaching AV node 52 are delayed by the junctional fibers connecting the node to the atrial wall and are also delayed by the AV node itself. The delayed action potentials leaving AV node 72 pass quickly through transitional fibers 74, and AV bundle 76 and the remainder of the Purkinje fibers to cause substantially simultaneous contraction of the ventricular muscles. Abnormalities of, or pressure on, the bundle of His may cause Stokes-Adams syndrome. Furthermore, the bundle of His including node 72, fibers 74, and bundle 76 is the most common location for ectopic foci which result in Wolff-Parkinson-White syndrome. Consequently, ablation of a portion of the bundle of His may be therapeutically desirable.

FIG. 2a illustrates an apparatus for radio frequency (RF) or microwave ablation of the bundle of His or of ectopic foci in the heart. In the semipictorial diagram of FIG. 2a, an elongated catheter designated generally as 208 is formed from a miniature coaxial cable (coax) 210 including a flexible center conductor 212 coaxial with a flexible outer conductor 214 having a circular cross section. A flexible insulating dielectric material illustrated as 216 extends through coaxial cable 210 in order to electrically insulate center conductor 212 from outer conductor 214 throughout its length and to establish a uniform spacing between the center and outer conductors. A suitable type of coaxial transmission line is type RG9178 manufactured by Alpha Wire Corp. the address of which is 711 Lidgerwood Avenue, Elizabeth, N.J. 07207. This cable has an overall diameter of 0.095 inches (2.413 mm). The center conductor is stranded. The thickness of the polytetrafluoroethylene (TEFLON) insulation between center and outer conductors is 0.012". An outer jacket of similar material surrounds the outer conductor. This type of coax can be cold gas sterilized. It has an attenuation of approximately 29 dB/100 feet at 400 MHz.

As illustrated, coaxial cable 210 is terminated at its distal end 220 in an antenna designated generally as 215. In FIG. 2a, antenna 215 includes a portion of center conductor 212 which extends at distal end 220 of coax 210 past the end of outer conductor 214. If coax is used to form the antenna 215 and has a multistrand center conductor, it is desirable to silver-solder or braze together the strands near the protruding tip to prevent their separation. As is well known in the electrical arts, the extension of center conductor 212 past the end of outer conductor 214 forms, together with a portion of outer conductor 214 near the distal end of coax 210, an antenna capable of radiating electromagnetic energy. At the proximal end 222 of catheter 208 and coax 210, the coaxial transmission line terminates in a standard coaxial connector illustrated schematically as 224. Coaxial connector 224 mates with a corresponding coaxial connector 226, the center conductor of which is electrically connected to a junction point 228 and the outer conductor of which is connected to a point of reference potential illustrated as ground. Junction point 228 is connected by way of a low pass filter illustrated as 230 to a conventional electrocardiograph or other display and recording apparatus 234 for displaying and/or recording action potentials from catheter 208 and from other electrodes illustrated as electrical conductors 236. Junction 228 is also coupled by means of a high pass filter illustrated as 240 to an adjustable or variable signal attenuator 242 which receives radio frequency or microwave signals from a source 244. FIG. 2b illustrates the transmission characteristics of filters 230 and 240.

In FIG. 2b, plot 260 represents the transmission characteristics of low pass filter 230. Plot 260 includes a flat-topped portion extending from zero frequency to a frequency $f_1$, representing passage of all signals from node to 228 to display and recording apparatus 234 at frequencies between zero and frequency $f_1$. Plot 260 also includes a sloped portion extending from frequency $f_1$ to $f_2$, representative of a decreasing transmission from junction point 228 to display and recording apparatus 234 with increasing frequency in the interval from $f_1$ and $f_2$. Above frequency $f_2$, no energy is transmitted from junction point 228 to display and recording apparatus 234. FIG. 2b also includes a plot 262 including a flat topped portion extending above frequency $f_4$, representing complete transmission from attenuator 242 to junction point 228 by way of high pass filter 240 of signals at frequencies above frequency $f_4$. The sloped portion of plot 262 represents a declining transmission of filter 240 as the frequency of signals decreases from $f_4$ to $f_3$, and no transmission of signals from attenuaton 242 to junction point 228 of signals below frequency $f_3$. The cutoff frequency $f_1$ of low-pass filter 230 is selected to be above 10,000 Hertz (Hz) in order to provide full bandwidth for display of action potentials of the heart. In order to provide maximum attenuation of the signals from source 244, the cut-off frequency should not be to far above 10,000 Hz. The arrangement of FIG. 2a with filter characteristics as represented by FIG. 2b allows catheter 208, when antenna 215 at its distal end 220 is inserted into a chamber of the heart and in contact with a wall of the heart, to conduct to junction 228 and through low-pass filter 230 to display and recording apparatus 234 the action potential of the muscles with which antenna 215 is in contact. The arrangement of FIG. 2a allows simultaneous display of action potentials and application of radio frequency or microwave power from signal source 244 through attenuator 242, through high-pass filter 240, past junction point 228 and into coaxial transmission line 210 to antenna 215. The RF or microwave signals are applied without affecting the display of action potentials.

In order to prepare the patient for treatment by a method of the invention, display and recorder apparatus 234 is connected by leads 236 to electrodes suitably placed on or in the body of the patient. The locations of the electrodes 236 are selected to provide an indication of the action of the heart.

Figure 3:
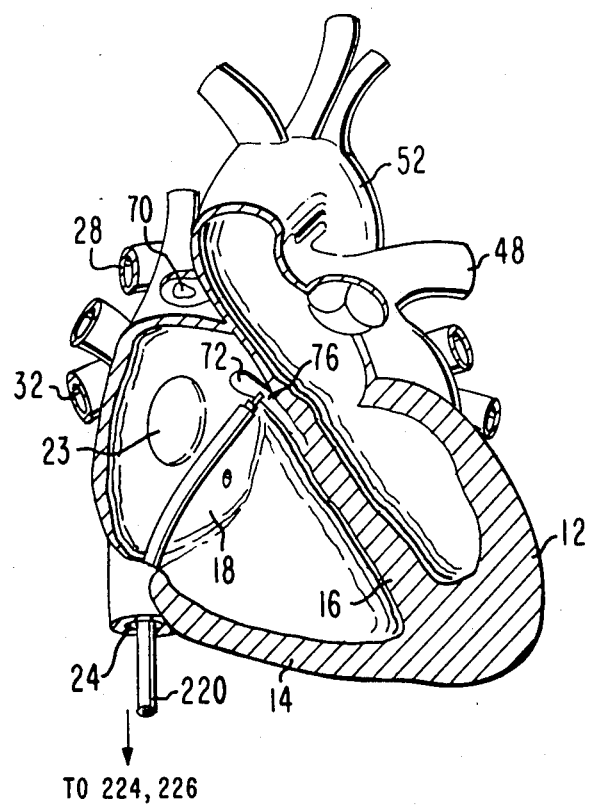
FIG. 3 is a sectional view of a heart showing the location of the catheter of the arrangement of FIG. 2a for ablation of the bundle of His.

FIG. 3 illustrates the location of the distal end 220 of coaxial cable 210 according to one method of treatment. As illustrated in FIG. 3, the distal end of coaxial cable 210 is introduced through the lumen of the inferior vena cava 24 in a manner well known in the art and is then adjusted in position so that antenna 215 (the protruding end of center conductor 212) contacts a point on the wall of the atrium. Beginning at the moment that a portion of antenna 215, namely the protruding end of center conductor 212, touches the wall of the atrium, the action potential at that point will be conducted through center conductor 212, connectors 224 and 226, past junction 228 and through low-pass filter 230 to display and recording apparatus 234. Since inner conductor 212 provides only one contact to the wall of the chamber, the biphasic action potential at that point may be established by comparison with the voltage on any of the leads 236 or with a common point derived from the leads 236, all in known fashion. Comparison of the signal derived from center conductor 212 of coaxial transmission line 210 with the other action potentials displayed by apparatus 234 provides an indication which aids in the accurate placement of the tip of exposed center conductor 212 at the appropriate point along the bundle of His. The exposed center conductor may be placed either at the AV node 72 or at any point between the AV node and ventricular septum 16. If the bundle of His is to be blocked, it is desirable to block as close to AV node 72 as possible, to make the remainder of the bundle of His downstream (in the direction of normal flow of the action potentials along the fiber) from AV node 72 available as a possible focus for ventricular pacemaking. In the case of an ectopic focus in the bundle of His itself, the protruding end of center conductor 212 should be located contiguous with (directly on or immediately adjacent to) the focus. Further details of the placement of the antenna are described in conjunction with FIG. 4. Once the antenna is contiguous with the area to be injured or ablated, power source 244 is energized, or if power source 244 is already energized the attenuation of attenuator 242 is reduced to allow a significant flow of energy through filter 240, connectors 234 and 236 and coaxial transmission line 210 to antenna 215. Energy is applied while observing the action potentials on apparatus 234. In order to block the bundle of His with minimal destruction of adjacent tissue, the attenuation of attenuator 242 is gradually reduced, allowing an increasing amount of radio frequency or microwave electrical power to flow from source 244 through coaxial transmission line 210 to antenna 215 and to the region of the bundle of His adjacent the antenna. As the power increases, it is believed that the temperature of the cells in the vicinity of the antenna rises due to absorption of energy. At a critical temperature near 43 to 45 degrees Celsius, the cells die quickly. However, the heating effect depends upon the power density of the electromagnetic signal in the vicinity of the tissues. Therefore, the extent of the region affected can be controlled by regulating by means of attenuator 242 the amount of power radiated by the antenna. The slow increase in power allows sufficient time for a steady thermal state to occur and for those tissues at temperatures above the critical temperature to die. The power is slowly increased until blockage begins to occur as indicated on display and recorder apparatus 234. The increase in power is then stopped and the power is maintained while blockage becomes complete. When blockage is complete, source 244 is turned off, or the attenuation of attenuator 242 is increased to a maximum. It may be desirable to maintain antenna contact at the same point on the bundle of His for a period of time after power is removed to verify that the blockage is complete and that transmission through the bundle of His will not resume. It may also be desirable to maintain the maximum power level for a period of time after full blockage occurs to assure that the conduction of action potentials by the last cells to be affected has not ceased solely due to injury but through actual death of the cell.

In a particular procedure according to the invention, a catheter similar to that of FIG. 2a had the following characteristics:
Cable: Alpha type 9178B Cable
Cable Diameter: 0.095 inch (2.413 mm)
Length of protruding center conductor: 0.075 inches (1.905 mm).

The proximal end of the catheter was connected to a display and recording apparatus and to a source of energy capable of producing several watts at 925 MHz. The distal end of the catheter and its associated antenna were introduced into a chamber of the heart of a live dog, and the bundle of His was located. A power of about one watt was applied for approximately 30 seconds, and some damage to the bundle of His was noted as indicated by the displayed action potentials. Power was increased to about 2 watts over an interval of about 30 additional seconds, whereupon blockage was complete. The procedure was then terminated. During the procedure, no undesired modes such as flutter or fibrillation occurred.

In order to avoid the possibility of inadvertently subjecting the patient to an excessively high radio frequency or microwave power level, it may be desirable to preset the levels of signal source 244 and signal attenuator 242, and to electrically connect the output of attenuator 242 to filter 240, as by operating a switch, (not illustrated in FIG. 2) when power is to be applied to the patient by way of catheter 208. When this method is used, power at the predetermined level can be applied to the desired position in the heart until blockage is achieved.

The antenna arrangements illustrated in FIGS. 2 and 4, and also in FIGS. 5 and 6, radiate a principal proportion of their energy in a direction radial to the axis of the coaxial transmission line, and radiate very little in an axial direction. FIG. 4 illustrates the preferred orientation of the antenna adjacent the bundle of His for blocking. As illustrated in FIG. 4, arrows 410 and 412 indicate the preferred radial direction of radiation of antenna 215 relative to a coaxial transmission line. With the illustrated orientation of cable and antenna relative to a portion designated 420 of the bundle of His, arrow 410 indicates the direction into the tissue taken by a portion of the radiated energy. Also indicated in FIG. 4 is the normal direction of flow of the action potential, which is from left to right. With the illustrated orientation, energy flowing from the antenna in direction 410 tends to destroy cells upstream from the point of contact 430 of the antenna with the bundle of His. Consequently, the action potentials coupled through center conductor 212 to display and recording apparatus 234 will be stopped when the bundle has been blocked. When an independent rhythm is assumed by the ventricles, the new lower beat rate will arrive at the antenna from the right and will be displayed. For a normal direction of flow of action potentials opposite to that illustrated, (i.e. from right to left) the blockage would occur downstream from the point of contact of the antenna, and therefore there would be no indication of when the blockage occurs; it would then be necessary to rely on indications from other electrodes to determine the fact of blockage. If the power is applied for a sufficiently long period of time or if a sufficiently large power is applied, cell destruction by radiation and direct conduction will be more generalized, and those cells near the point of contact with the antenna will be destroyed by the relatively high current levels. Thus, at sufficiently high power levels the orientation of the antenna is irrelevant.

Figure 6A:
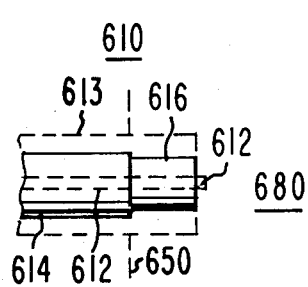
FIGS. 6a and 6b illustrate additional types of antennas which may terminate the coaxial transmission line.

FIGS. 5 a,b and c illustrate various antenna shapes. Such antenna shapes are advantageous in that they tend to increase the capacitance between the tip of the radiating element and the end of the outer conductor and thereby provide a high current density along the radiating element. This arrangement is known as "end loading" of an antenna element. Such shapes are less well adapted to catheter use than the antennas illustrated in FIG. 6. In FIG. 6a, a coaxial transmission line designated generally as 610 has an outer conductor 614 which ends at a plane 650. A center conductor 612 coaxial with outer conductor 614 is maintained in position coaxial with outer conductor 614 and insulated therefrom by insulation 616. Center conductor 612 extends past plane 650 for a predetermined distance as known to form an antenna designated generally as 680. Insulation 616 also extends past plane 650 almost to the end of center conductor 612. By comparison with the arrangement illustrated in FIG. 2a or in FIGS. 5a-c the arrangement of FIG. 6a provides a relatively long path between the exposed tip of center conductor 612 and the exposed portion of outer conductor 614, which reduces the likelihood of occurrence of arcs between center conductor 612 and outer conductor 614. The likelihood of an arc can be further reduced by a conformal insulating outer covering 613 covering all portions of outer conductor 614, insulator 616 and inner conductor 612 except for the small protruding portion as of center conductor 612 as illustrated.

Figure 6B:
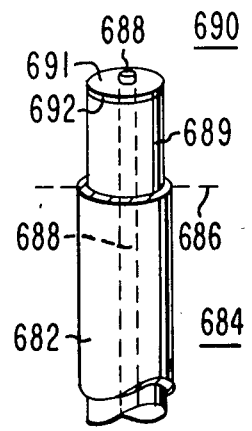

FIG. 6b illustrates an antenna arrangement combining the advantages of the arrangements of FIG. 5 and FIG. 6a. In FIG. 6b, an outer conductor 682 of a piece of coaxial transmission line is designated generally as 684 terminates at a plane indicated as 686. The center conductor 688 of coaxial transmission line 684 extends past plane 686 to form a principal radiating element of an antenna 690. The insulation 689 extends past plane 686 to provide an insulating sheathing about center conductor 688 almost to the protruding tip. Insulation 689 is cut so as to define a flat surface 691 surrounding the tip of center conductor 688. As illustrated in FIG. 6b, flat surface 691 of insulation 689 is covered with a thin coating 692 of conductive material such as silver. The silver may be deposited on the surface of insulation 689 by sputtering or other known techniques. The arrangement of FIG. 6b is advantageous because it provides a blunt end for probing the walls of the heart chambers and thereby reduces the likelihood of traumatic injury to undesired portions of the heart, and it provides top loading for more effective radiation in a manner similar to that described in conjunction with the antennas of FIGS. 5. The arrangement of FIG. 6b also provides a relatively large gap between outer conductor 682 and the electrically exposed portions of conductor connected to center conductor 688 and thereby reduces the likelihood of arcing.

Figure 7:
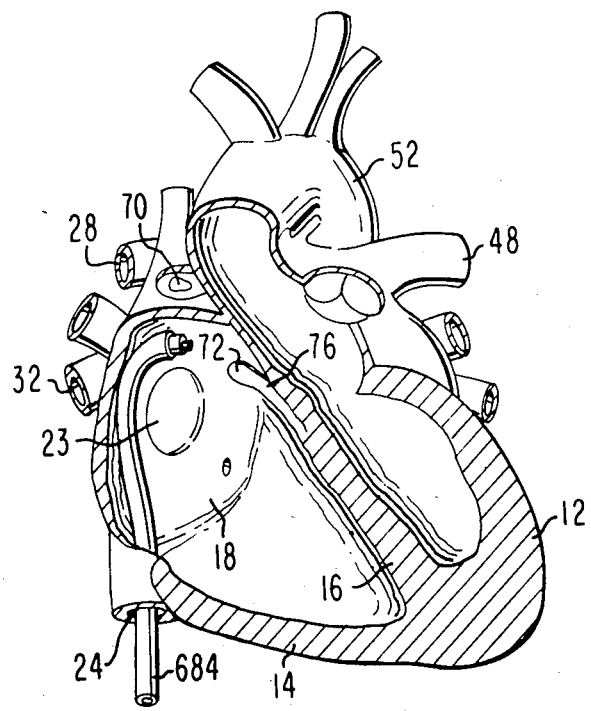
FIG. 7 illustrates a coaxial transmission line and antenna arranged for ablating an ectopic focus on the posterior wall of the atrium.

FIG. 7 illustrates an antenna similar to that illustrated in conjunction with FIG. 6 oriented adjacent an ectopic focus (not separately illustrated) in the vault of the atrium.

In the aforementioned Gillette article, Gillette notes that an intravascular electrode in the inferior vena cava gives superior electrical tracings for the bundle of His. A separate conductor may be introduced into the vena cava together with catheter 208 for obtaining this potential. Alternatively, the outer conductor 214 of catheter 208 may additionally be used as an electrode coupled to the inferior vena cava. This is accomplished by electrically insulating the outside of outer conductor 214 except in the region which is near the vena cava when the tip of antenna 215 is in contact with the bundle of His. The flexing of the cable will bring the uninsulated portion of the outer conductor into contact with the wall of the lumen of the vena cava. At the proximal end of the catheter, the outer conductor must be coupled by a low pass filter (not illustrated) to the appropriate terminal of display and recording apparatus 234, and coupled to the reference potential by a high pass filter element such as a capacitor (not illustrated).

Other embodiments of the invention will be apparent to those skilled in the art. If desired, the coaxial cable may be introduced into the body by means of a standard cannulla of suitable diameter. While the described apparatus monitors biphasic action potentials, the antenna of a catheter according to the invention may be used for monitoring monophasic action potentials. While simple linear radiators have been illustrated as antennas, there is in principle no reason that more complex or multielement directive antennas could not be used, so long as they will fit into a catheter.

What is claimed is:

1. A method for medical treatment, comprising the steps of:
   introducing into a chamber of the heart one end of a coaxial transmission line which includes a center conductor coaxial with an outer conductor, said one end of said coaxial transmission line including an antenna coupled to said center conductor, said antenna including an uninsulated protruding tip;
   adjusting the position of said one end of said protruding tip of said antenna contacts a wall of said coaxial transmission line in such a fashion that said chamber for coupling to said antenna action potentials related to the operation of the heart;

coupling to the other end of said coaxial transmission line a means for displaying said action potentials;

displaying said action potentials;

further adjusting the position of said one end of said coaxial transmission line so as to be contiguous with that point on said wall with a desired action potential;

continuously applying high frequency electromagnetic energy to said other end of said coaxial transmission line during a period of time;

observing action potentials related to operation of said heart at least during said period of time;

monotonically increasing the power of said electromagnetic energy during said period of time; and ceasing said increasing and terminating said period of time when said action potentials are reduced.

2. A method according to claim 1 wherein said coupling step comprises the steps of:

coupling to the body of the patient one or more additional conductors for sensing action potentials attributable to operation of said heart; and coupling to said center conductor of said other end of said coaxial transmission line and to said one or more additional conductors a comparison means for generating and displaying as said action potentials the voltage between said center conductor and at least one of said one or more additional conductors.

3. A method according to claim 1 wherein said step of displaying said action potentials includes a recording step.

4. A method for therapeutic blocking of the bundle of His, comprising the steps of:

introducing into the right atrium of the heart one end of a coaxial transmission line which includes coaxial center and outer conductors, said one end of said coaxial transmission line having an antenna including an exposed tip coupled to said center conductor;

adjusting the position of said one end of said coaxial transmission line in such a fashion that said exposed tip contacts a wall of said atrium for coupling to said center conductor action potentials related to the operation of the heart;

coupling to the other end of said coaxial transmission line a means for displaying said action potentials;

displaying said action potentials;

further adjusting the position of said one end of said coaxial transmission line so that said antenna is contiguous with a point from which the displayed action potentials are characteristic of a desired portion of the bundle of His;

continuously applying high frequency electromagnetic energy to said other end of said coaxial transmission line;

observing said action potentials of said desired portion of said bundle of His while performing said continuously applying step;

increasing the power of said electromagnetic energy during said observing step; and ceasing said increasing when said action potentials are sufficiently reduced.

5. A method according to claim 4 wherein said coupling step comprises the steps of:

coupling to the body of the patient one or more additional electrodes for sensing action potentials attributable to operation of said heart; and coupling to said center conductor of said other end of said coaxial transmission line and to said one or more additional electrodes a comparison means for generating and displaying as said action potentials the voltage between said center conductor and at least one of said one or more additional conductors.

6. A method according to claim 4 wherein said step of displaying said action potentials includes a recording step.

* * * * *

UNITED STATES PATENT AND TRADEMARK OFFICE
CERTIFICATE OF CORRECTION

PATENT NO. : 4,641,649

DATED : February 10, 1987

INVENTOR(S): Paul Walinsky, Arye Rosen, Arnold J. Greenspon

It is certified that error appears in the above-identified patent and that said Letters Patent is hereby corrected as shown below:

Col. 8, line 64, insert before "protruding" --coaxial transmission line in such a fashion that said--.

Col. 8, line 65, delete "coax-".

Col. 8, line 66, delete "ial transmission line in such a fashion that said".

Signed and Sealed this

Sixth Day of October, 1987

Attest:

Attesting Officer

DONALD J. QUIGG

Commissioner of Patents and Trademarks